(12) United States Patent
Breznock et al.

(10) Patent No.: US 7,935,102 B2
(45) Date of Patent: May 3, 2011

(54) METHOD AND APPARATUS FOR PREVENTION OF CATHETER AIR INTAKE

(75) Inventors: Eugene M. Breznock, Winters, CA (US); Jay A. Lenker, Laguna Beach, CA (US); David W. Wieting, Fredricksburg, TX (US)

(73) Assignee: Indian Wells Medical, Inc, Laguna Beach, CA (US)

( * ) Notice: Subject to any disclaimer, the term of this patent is extended or adjusted under 35 U.S.C. 154(b) by 0 days.

(21) Appl. No.: 12/317,127

(22) Filed: Dec. 19, 2008

(65) Prior Publication Data

US 2009/0163864 A1 Jun. 25, 2009

Related U.S. Application Data

(60) Provisional application No. 61/008,952, filed on Dec. 21, 2007, provisional application No. 61/069,979, filed on Mar. 19, 2008.

(51) Int. Cl.
*A61M 31/00* (2006.01)
*A61M 1/00* (2006.01)

(52) U.S. Cl. ..................................... 604/508; 604/122
(58) Field of Classification Search .................. 604/118, 604/119, 121, 122–127
See application file for complete search history.

(56) References Cited

U.S. PATENT DOCUMENTS

| | | | |
|---|---|---|---|
| 3,768,726 A | 10/1973 | Hale et al. | |
| 4,682,980 A | 7/1987 | Suzuki | |
| 5,662,611 A * | 9/1997 | Beiser et al. | 604/118 |
| 5,823,986 A | 10/1998 | Peterson | |
| 5,823,987 A | 10/1998 | Elgas et al. | |
| 6,224,829 B1 | 5/2001 | Piplani et al. | |
| 6,245,045 B1 | 6/2001 | Stratienko | |
| 6,264,601 B1 | 7/2001 | Jassawalla et al. | |
| 6,769,871 B2 | 8/2004 | Yamazaki | |
| 2002/0110485 A1 | 8/2002 | Stringer et al. | |
| 2005/0027253 A1* | 2/2005 | Castellano et al. | 604/122 |
| 2005/0192525 A1* | 9/2005 | Wieting et al. | 604/6.09 |
| 2006/0084836 A1 | 4/2006 | Hubbard et al. | |

FOREIGN PATENT DOCUMENTS

WO WO 2005/056094 6/2005
WO WO 2007089309 A2 * 8/2007

* cited by examiner

*Primary Examiner* — Nicholas D Lucchesi
*Assistant Examiner* — Jenna Zhang
(74) *Attorney, Agent, or Firm* — K. David Crockett, Esq.; Crockett & Crockett, PC (57) ABSTRACT

A system for preventing air from entering a first catheter of a multi-catheter system. Air is prevented from entering the proximal end of the first catheter by an axially elongate chamber having an impeller, the chamber being affixed to the proximal end of the first catheter. The air is removed through a port near the centerline of the chamber. Liquid removed with the air is returned to the chamber to minimize liquid loss during the procedure. A second catheter inserted through the chamber and into the first catheter is unable to entrain gas into the first catheter because any gas that enters the chamber is routed to the centerline of the chamber where it is removed. Inflow of fluid from an external pump scrubs the second catheter shaft of air bubbles attached by surface tension.

8 Claims, 10 Drawing Sheets

METHOD AND APPARATUS FOR PREVENTION OF CATHETER AIR INTAKE

PRIORITY CLAIM

This application claims priority benefit under 35 USC §119(e) from U.S. Provisional Application No. 61/008,952, filed Dec. 21, 2007, entitled METHOD AND APPARATUS FOR PREVENTION OF CATHETER AIR INTAKE, and U.S. Provisional Application No. 61/069,979, filed Mar. 19, 2008, entitled METHOD AND APPARATUS FOR PREVENTION OF CATHETER AIR INTAKE the entire contents of both of which are hereby incorporated herein by reference.

FIELD OF THE INVENTION

The field of this invention is cardiology, radiology, electrophysiology, or endovascular surgery, and more particularly the fields of cardiac or circulatory system catheterization.

BACKGROUND OF THE INVENTION

Catheters are introduced into the cardiovascular system for various diagnostic and therapeutic reasons. Catheters are often introduced into the cardiovascular system through introduction sheaths that provide a pre-determined conduit from the access site to the treatment site and facilitate vascular access of new catheters as well as the exchange of catheters within the vasculature. Such catheters and introducer sheaths are used in both the arterial, higher pressure, circulation and the venous, lower pressure, circulation. Introducer sheaths suitable for guiding devices through the vasculature and into the right or left atrium of the heart are prime examples of such vascular access.

The introducer sheaths and catheters used for these purposes are generally primed with saline and purged of any air prior to being inserted into the patient's cardiovascular system through a percutaneous or open surgical access to an artery or vein. The purpose of purging air from a catheter or introducer sheath is to prevent that air from inadvertently being forced, under a pressure drop generated within the catheter or sheath, out the distal end of the catheter and into the patient's circulatory system.

The act of inserting a therapeutic or diagnostic catheter through an introducer sheath can cause air or other gas to be introduced into the central lumen of the introducer sheath. Such air can migrate distally into the patient's cardiovascular system under certain circumstances, especially when the distal end of the introducer sheath is located within the venous side of the cardiovascular system or in the left atrium of the heart. In certain pathological and physiological states, relatively low pressures can exist within the venous side of the heart with a pressure gradient existing between the right and left atrium. Such gradients in the presence of a Patent Foramen Ovale (PFO), a not uncommon congenital cardiac condition, can easily result in air emboli traversing from the right heart to the left heart during right heart interventional procedures. In addition, these relatively low pressures can exist for a non-trivial portion of the cardiac cycle resulting in the potential for a negative pressure gradient between the room pressure, which in a clean room, catheterization lab, or surgical suite is generally slightly elevated, and the distal end of the introduction sheath. There is a potential for any gas or air entrained into the proximal end of the introduction sheath to migrate out the distal end of the introduction sheath and into the patient's cardiovascular system where it could cause an air embolism. During a portion of the cardiac cycle, pressures within the left atrium can approach very low values and can even go negative relative to room pressure.

The clinical ramifications of an air embolism range from no noticeable effect to cerebrovascular stroke or cardiac ischemia, either of which could have mild to severe outcomes and could even result in patient death. Air can also be entrained out the distal end of the sheath by surface tension forces between the catheter and the air. This surface tension can cause the air to adhere to the catheter while it is advanced out the distal end of the sheath. Thus, any air that inadvertently enters the sheath or catheter system is at risk for introduction to the patient, an event with potentially catastrophic consequences such as cerebrovascular embolism, coronary embolism, and the like. Air embolism is clearly an issue especially with catheters directed toward the cerebrovasculature or the coronary circulation, but also with catheters or sheaths directed anywhere within the circulatory system of the mammalian patient.

New devices and methods are needed to more efficiently remove gas that inadvertently migrates into a catheter or sheath so that it is prevented from being routed into the patient's cardiovascular system. The need has been heightened by recent Medicare regulations that restrict or deny reimbursement for certain hospital acquired conditions including air embolism.

SUMMARY OF THE INVENTION

This invention relates to a blood filter, blood-air filter, or trap for removing air or other gas from the fluid within a primed introducer sheath, catheter, or similar device placed anywhere within the cardiovascular circuit of a patient. The liquid fluid within a cardiovascular catheter or sheath can comprise blood, blood products, water, sodium chloride, various pharmacologic agents, and the like. In some embodiments of the inventions, the device or apparatus comprises a chamber or housing with a catheter inlet port and a catheter outlet port, the catheter outlet port being connected to the proximal end of an introduction sheath, or first catheter. In addition, the chamber has a third outlet port for removing gas from the liquid. The device additionally comprises a stirring rod or impeller to spin the blood circumferentially within the chamber. This stirring rod or impeller is coupled to a rotary motor that generates the rotational energy necessary to separate gas from the blood by buoyancy, or centripetal effects. The less dense bubbles move toward the center of the rotating fluid field while the more dense liquid is moved to the periphery of the rotating fluid field. The faster the fluid field rotates, the more quickly the air is separated from the liquid. The present inventions actively remove gas and debris from the catheter, including both tiny gas bubbles and large boluses of gas. The inventions can strip gas or air bubbles, attracted to a secondary catheter inserted through the chamber by surface tension effects or similar forces, away from the secondary catheter and into a rotational flow field where the gas can be actively removed from the chamber. The gas has less mass than the same volume of blood or saline, i.e. the bubbles are buoyant in the liquid, so that rotation causes them to move toward the center of the liquid filter by centripetal force. The centripetal force accelerates the gas until the bubbles reach an axially inward radial velocity where the drag force balances the centrifugal force and the bubbles move toward the center of rotation of the device.

In some embodiments, the invention actively rotates the blood or other liquid within a chamber to drive gas toward the center of the chamber under centrifugal forces interacting with buoyant forces on the gas, and allows separation of the blood or other liquid from the aforementioned gas. The gas is removed from the chamber of the device through a gas vent, approximately aligned with the axis of rotation, where the air is stored in a gas reservoir, while any liquid is pumped back into the chamber of the device. The gas trap or filter of the present invention is designed to remove the majority of air bubbles and prevent those air bubbles from entering or escaping the distal end of the catheter or sheath.

In some embodiments, the axis of the chamber, and the axis about which the impeller rotates, is aligned parallel to the longitudinal axis of the catheter or sheath to which it is affixed. In another embodiment, the chamber is aligned with its rotational axis lateral to that of the catheter major axis. In this embodiment, rotational fluid flow is less restricted by the presence of a catheter being inserted along the longitudinal axis of the sheath because the inserted catheter, which passes through the chamber is aligned generally in the direction of the rotational fluid flow and not transverse thereto.

In another embodiments, the chamber does not comprise an impeller but the chamber comprises an inlet seal or valve that separates the chamber from the outside environment, an optional outlet seal or valve that separates the chamber from the distal end of the first catheter or sheath, an outlet port for air and a return port for liquids. The inlet seal or valve and the outlet seal or valve serve to trap any air within the chamber so that the air cannot pass into the proximal end of the sheath or catheter through the outlet valve or seal. The chamber further comprises an external fluid pump, air reservoir, return line, and electrical power source.

In some embodiments, a filter is described that is affixed or integral to the proximal end of an introducer or introduction sheath. The filter is completely self-contained, small, and non-bulky. The filter, including all components, can be contained or integrated within a shell. The filter, including all components, can be contained either within a shell or within modules directly affixed to the shell. In certain embodiments, the filter is a unitary or integral structure with no wires, lines, tubes, or other flexible linkages extending therefrom. The filter system does not require a hanging bag or reservoir of saline or other liquid since it gets its fluid from the catheter itself. The filter is capable of being maneuvered at the proximal end of the sheath and allows therapeutic or diagnostic catheters to be passed therethrough on their way into the sheath or introducer. Thus, all components or modules are integral to, or affixed to, the filter unit. The components or modules can all be integrated within or housed within a single shell, casing. This is extremely important so that the filter assembly does not render the sheath or catheter system unwieldy, awkward, or unbalanced. In certain embodiments, the chamber, the return line, the air separation chamber, the pump, the pump motor, the battery, any inlet and outlet valves, and all interconnecting components are integral to or affixed to each other. The components can be rigidly or flexibly affixed to each other. The battery can comprise chemistries such as, but not limited to, alkaline, lithium, lithium ion, nickel metal hydride, lead acid, and the like. Battery operating voltages can range between 1.25 and 12 volts with a preferred range of between 3 and 7 volts. Computers, controllers, and other circuitry can be used to monitor motor function, presence of gas via ultrasound transducers, battery power, and the like. The controllers can further comprise circuitry, software, or both to process the information and provide warnings to the user.

In accordance with another aspect of the invention, a method is described to remove gas from an axially elongate chamber affixed to the proximal end of an introducer, first catheter, or introduction sheath. This method includes the step of affixing the chamber to the proximal end of the first catheter or sheath such that the first catheter or sheath is connected near the radial periphery of the chamber. Next the method includes spinning the fluid, blood, saline, air, and the like, within the chamber about a central axis by means of an impeller at high rotational rates to move the gas to the center, or axis of rotation, of the chamber and away from the first catheter or sheath port to a gas removal port located generally near the axis of rotation within the chamber where the gas is removed. In a further aspect of the invention, the air or gas removed from the fluid at or near the center of the chamber is separated from the liquid in an external gas separation chamber and the liquid is ultimately returned to the chamber or the patient. In an embodiment, the same impeller that spins the blood within the chamber can be used to pump the liquid back into the chamber. In another embodiment, a separate impeller or pump can be used to move the liquid back into the chamber. In another embodiment, the same motor but different impellers or pumping devices can be used to spin the blood and move the blood through the system.

In other embodiments, the chamber is configured so that fluid, blood, air, non-cellular prime, or the like, are pumped out of the chamber where the air is separated from the liquid, and the liquid is returned to the chamber. In yet another embodiment, entry and exit valves are provided at the proximal and distal end of the chamber. These entry and exit valves minimize the amount of fluid, either air or liquid that can escape therethrough, with or without a secondary catheter having been passed through these valves. In some embodiments, the return line to the chamber is aligned tangentially to the circumference of the chamber such that the return flow generates rotational flow within the chamber that strips air from a secondary catheter inserted therethrough and drives the air toward the center of the chamber where it is drawn off. In some of these embodiments, the chamber is aligned with its axis of rotation vertical so that the air or gas directed toward the center can rise and be removed out the exit vent from the chamber. In some embodiments, the top of the generally cylindrical chamber can have a domed, funnel, or otherwise tapered shape to coerce gas and air toward the center, where the fluid exit from the chamber is located.

The present inventions distinguish over the cited prior art because they use an active component, or tangential return flow jet, to spin the liquid to forcibly remove gas and gas bubbles from the blood, catheter prime, saline, or other liquid. The invention is most useful during endovascular surgery, interventional neuroradiology procedures, interventional cardiology procedures, electrophysiology procedures, and the like. The invention does not block air from entering a bubble filter chamber by application of high pressure but rather quickly removes air entrained into the chamber away from the catheter where it can be pulled off and separated from any liquid, thus allowing the air-free liquid to be returned to the system. The system also has the advantage, due to the high rotational velocity of the liquid within the chamber, of being able to scrub any air away from a second catheter inserted through the chamber, wherein the air is adherent to the catheter by surface tension effects.

In another embodiment of the invention, an ultrasound transducer is affixed to the chamber and the ultrasound transducer is connected to control circuitry such that the presence of air can be detected and a warning device such as an audible bell, buzzer, a visible light or warning device, or the like can be activated to alert the operator that air is within the system and that caution should be maintained or corrective steps applied. The ultrasound transducer can be made to monitor the chamber inlet, the chamber, outlet, or both such that, in an embodiment, the warning signal only occurs if air nears the outlet of the chamber, where it could potentially pass into the first catheter or sheath. Once the gas or air is detected, system checks can be performed to prevent any flushing of fluid and air, within a guide sheath and/or catheter, into the patient.

In other embodiments of the invention, the system is self-priming and withdraws liquid retrograde through the sheath and into the bubble filter such that it does not require a separate source of liquid or fluid. Such separate sources of liquid or fluid, which are not required for the present device or method, can include bags or reservoirs of fluid hung beside the patient. In some embodiments, the system comprises a valve at its proximal end but not at its distal end. In other embodiments, the system comprises a valve at both the proximal end and the distal end. The valve can be a hemostasis valve of the type including, but not limited to, a duckbill valve, a pinhole valve, a slit valve, a Tuohy-Borst valve, and the like. Any valves located at the distal end of the bubble filter are preferably able to permit retrograde flow therethrough, even with a secondary catheter inserted therethrough. Such retrograde flow capability facilitates priming of the filter with blood withdrawn from the patient. Any valves located at the proximal end of the bubble or air filter preferably seal both in the antegrade and retrograde directions.

In other embodiments, an external bubble collection system is provided outside the bubble or air filter. Air removed from the air or bubble filter main chamber, through which the secondary catheter passes, is moved through the external bubble collection system. The external bubble collection system can comprise a mesh filter having a pore size of about 25 microns and can further comprise a gravity separator to remove air from a high port while blood or non-cellular liquids are removed through a lower port. The external bubble collection system can further comprise a membrane filter operating under pressure to separate gas from liquid.

The present invention distinguishes over the cited prior art because it uses an active component to spin the blood to forcibly remove gas bubbles from the blood. The invention is useful during cardiovascular catheterization procedures, especially those accessing the left atrium, the venous circulation, and the cerebrovasculature. The device is also useful during surgery when cardiopulmonary bypass is instituted to maintain the patient on temporary cardiopulmonary support. It is also useful for removal of gas and bubbles during intravenous infusion of liquids to a patient. Patients with increased risk of pulmonary emboli are especially vulnerable during intravenous infusion and would benefit from such protection.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE INVENTIONS

As used herein the terms distal and proximal are used to clarify the location of various points along the axial length of a catheter or sheath. Points are defined with respect to the end grasped by the user and the end that is inserted in the patient in the same manner as would one skilled in the art of medical device catheter construction. The proximal end of the catheter or sheath is defined as that end closest to the user or operator, or user, of the catheter or sheath while the distal end of the catheter or sheath is defined as that end that is inserted into the patient.

Figure 1A:
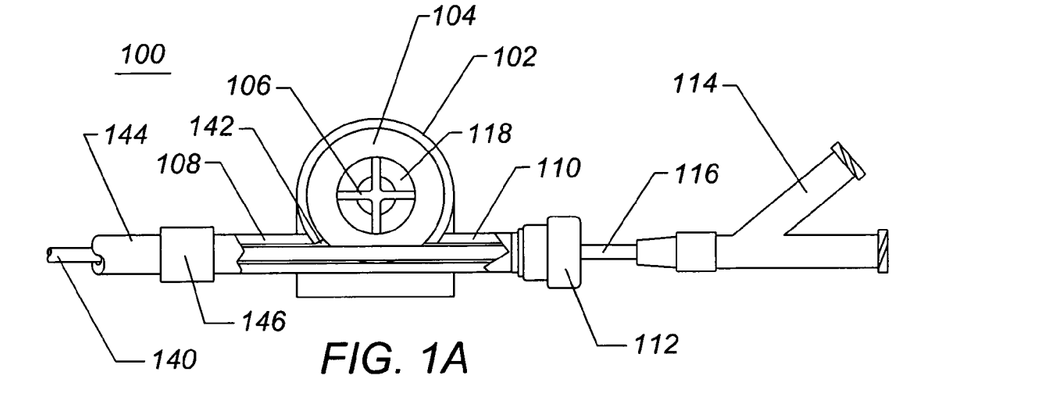
FIG. 1A illustrates a breakaway side view of a catheter air removal filter, integrated to the proximal end of an access sheath, catheter, or cannula, wherein the filter comprises a chamber, an impeller within the chamber, an inlet seal or valve, and a motor to drive the impeller, according to an embodiment of the invention.

FIG. 1A illustrates a side view of a catheter blood air filter assembly 100 of the present invention. The filter assembly 100 comprises a shell 102 further comprising an internal chamber 104, and an impeller 118 further comprising a plurality of vanes 106. The filter assembly 100 further comprises a second catheter inlet port 110, a second catheter outlet port 108, an inlet hemostasis valve 112, an optional outlet hemostasis valve (not shown), a gas vent (not shown), a motor drive (not shown), an electrical power source (not shown), a gas separator chamber (not shown), an on-off switch (not shown), a power cable connecting the electrical power source and the motor drive (not shown), and a return liquid port (not shown).

The shell 102 is configured with an axis of rotation about which fluid within the shell 102 can rotate. Therefore the shell 102 is approximately round in internal cross-section with the chamber 104 having a generally axially elongate cylindrical shape. The impeller 118 is affixed to the shaft of the motor drive (not shown) and rotates about the shaft axis at speeds between approximately 10 and 5000 revolutions per minute (RPM), and preferably between 100 and 1000 RPM. The primary concern is for removal of larger air bubbles that can be easily moved to the center of the device at these rotational rates, even if the device is flipped sideways, upside down, or any other orientation since the rotational, buoyant—forces will overpower gravitational at these rotation rates. The second catheter inlet port 110 is aligned generally tangential to the outer circumference of the chamber 104 and the lumen of the second catheter inlet port 110 is operably connected to the interior of the chamber 104. The second catheter outlet port 108 is aligned generally tangential to the outer circumference of the chamber 104 and is aligned generally coaxially with the second catheter inlet port 110. A second catheter 116, further comprising a second catheter hub 114 and a second catheter shaft 140, when inserted through the second catheter inlet port 110 can be advanced through the chamber 104 and into the second catheter outlet port 108 without restriction, binding, or obstruction. The entry 142 to the second catheter outlet port 108 from the chamber 104 can, in a preferred embodiment, be flared, beveled, or funnel shaped such that should the second catheter shaft 140 bend slightly out of the line of the straight axis, it will be coerced or guided into the second catheter outlet port 108.

The main axis, along which the second catheter 116 runs, can be oriented parallel to the rotational axis of the impeller 118 or, in a preferred embodiment, the catheter axis can be oriented perpendicular to the rotational axis of the impeller 118. The rotational axis of any fluid within the chamber 104 will be approximately the same as that of the impeller 118, since the impeller 118 directly drives the rotational motion of said fluid. By orienting the catheter 116 axis perpendicular to the rotational axis of the impeller 118, the blood and fluid within the chamber 104 will rotate generally in a similar direction as the axis of the second catheter shaft 140 as it passes the second catheter shaft 140 and thus flow disturbance by the catheter shaft 140 will be minimized. High velocity flow passing the second catheter shaft 140 will entrain any bubbles of gas attached thereto and drive the bubbles into the flow vortex created by the spinning impeller 118. The bubbles entrained in the flow vortex will migrate to the center of the vortex by buoyancy effects operating within the rotational flow field. Thus the lighter gas elements or bubbles will move inward while the heavier liquid and solid elements will move outward in the rotational flow field. The axis of rotation of the impeller 118 is preferably higher than the axis of the second catheter 116 so that passive buoyancy effects facilitate bubble separation from the region of the second catheter 116.

The shell 102 and the impeller 118 can be fabricated from polymers such as, but not limited to, polycarbonate, polysulfone, polyvinyl chloride, polyurethane, polyethylene, polyimide, polyamide, polyester, and the like. The shell 102 is preferably fabricated from a generally transparent polymer so that visualization of air or gas within the chamber 104 is possible. The diameter of the chamber 104 can range from about 0.5-cm to about 10-cm with a preferred diameter of about 2-cm to about 5-cm. The width of the chamber 104 along its rotational axis can range from about 1-cm to about 10-cm with a preferred range of about 2-cm to about 7-cm. The weight of the filter assembly 100 should be as low as possible so as to minimize forces on the first catheter or sheath 144 to which the filter assembly 100 is attached. The weight of the filter assembly 100 should be less than 450 grams and preferably less than 200 grams. The outlet port 108 of the filter assembly 100 can be attached to the first catheter or sheath 144 with a reversible coupling 146 such as a Luer lock, bayonet mount, screw thread, fastener, or the like, or it can be permanently affixed thereto. It is beneficial to use a locking type connector 146, or a permanent connection, to minimize the risk of the filter assembly 100 from inadvertently becoming disconnected from the first catheter or sheath 144 as air could then enter the first catheter or sheath 144, defeating the purpose of the filter assembly 100.

The valve 112 can be affixed, or integral, to the second catheter inlet port 110, which is affixed, or integral, to the chamber 104. The valve 112 can be a Tuohy-Borst valve, an elastomeric membrane with a pinhole, a duckbill valve, an elastomeric gasket with a central orifice slightly smaller than shaft 140 of the second catheter 116, or a combination of the these designs.

Figure 1B:
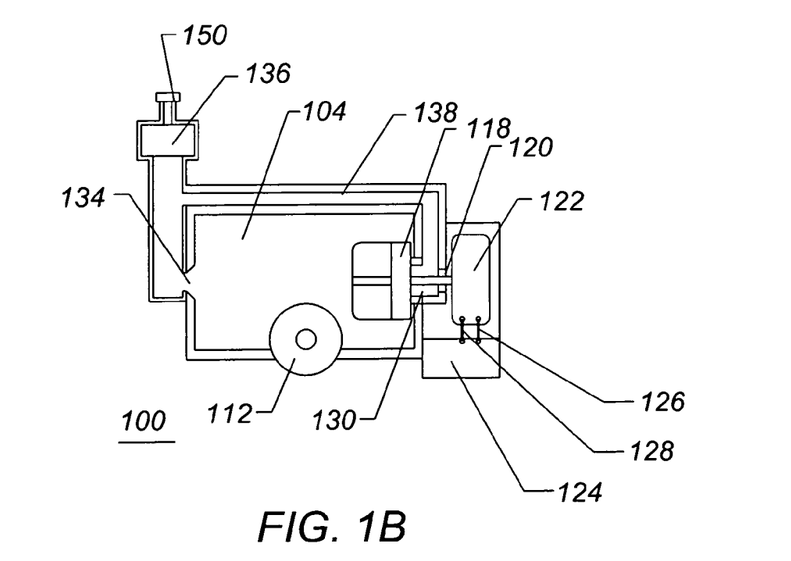
FIG. 1B illustrates a cross-sectional rear view of the catheter air removal filter of FIG. 1A showing the impeller, the motor, the batteries, the external gas separation chamber, and the liquid return line, according to an embodiment of the invention.

FIG. 1B illustrates the catheter blood air filter assembly 100 of FIG. 1A as viewed from the proximal end. The filter assembly 100 comprises the shell 102, the chamber 104, the impeller 118, the inlet valve 112, the gas removal port 134, the gas separation chamber 136, the liquid return line 138, the liquid return port 130, the motor bearing 120, the motor 122, the motor shaft 148, the electrical connections 126, 128, the battery 124, and an on-off switch (not shown).

Referring to FIG. 1B, the second catheter (not shown) has its axis aligned with that of the inlet valve 112. The motor is affixed to the impeller 118 by the motor shaft 148. The gas outlet port 134 is aligned generally along the rotational axis of the impeller 118 and allows air collected within the fluid vortex to escape from the chamber 104 and rise up into the gas separation chamber 136. Gas can be drawn off from the gas separation chamber 136 through the gas escape port 150, which is affixed to the top of the gas separation chamber 136 and operably connected to the internal volume of the gas separation chamber 136. The liquid return line 138 is affixed and operably connected to the bottom of the gas separation chamber 136 so that liquid can be returned back to the chamber by the action of the impeller 118, which not only generates rotational motion to the fluid within the chamber 104 but serves to drive fluids into the chamber 104 and toward the gas removal port 134.

The impeller 118 can be configured to drive forward flow by creating openings in the motor 122 side of the impeller 118 and beveling the surfaces around the openings to form propeller-type geometries within the impeller 118. Thus, a single motor 122 and impeller 118 can perform all the fluid forcing required by the filter assembly 100. In another embodiment, a second motor and pump (not shown), or at least a second pump (not shown) operated by the same motor 122 causes fluid flow within the liquid return line 138. Flow rates within the liquid return line 138 can range between 0.5-cc per minute and 100-cc per minute. A separate liquid infusion port (not shown) can be operably connected to a hanging bag or source of non-cellular prime (not shown) such as saline, but this is not required for operation of the filter assembly 100 since all liquid can be drawn from the catheter or the initial filter assembly priming step.

In an embodiment, the impeller 118 can be housed within the chamber 104 without any impeller or motor shaft 148 passing through the wall of the chamber 104. This can be performed by embedding permanent magnets within the impeller 118 and having the motor 122 and shaft 148 turn complementary permanent magnets, which are affixed thereto. These permanent magnets can engage the impeller, by means of magnetic fields, through the walls of the chamber 104 and generate rotational motion of the impeller 118. The magnetic field interacts with the magnets within the impeller 118 and causes the impeller 118 to rotate at the same rate as that of the motor 122. The magnetic driver (not shown) is preferably a bar magnet that spins about its central region with north and south poles diametrically opposed and equidistant from the center of rotation. Typical permanent magnets are fabricated from materials such as, but not limited to, neodymium iron boron, iron, ceramics, samarium cobalt and the like. Materials that are magnetically attracted to a magnet include, but are not limited to, iron or metallic alloys of iron. The magnetic driver (not shown) is desirable because it allows for a sealed chamber 104.

All components of the blood air removal system 100 can be fabricated preferably from biocompatible materials, which are sterilizable using either ethylene oxide, gamma irradiation, electron beam irradiation, or the like. The blood air removal system 100 can be provided separately for attachment to a first catheter or sheath 140, it can be pre-attached thereto, or it can be provided in a kit, separately attached but provided therewith. The blood air removal filter system 100 is preferably provided sterile in an aseptic packaging system (not shown).

Optionally, the interior of the shell 102 of the blood filter 100 can be treated or coated with an anti-thrombogenic material such as heparin and a bonding agent. The impeller 118 can be made from materials that include polycarbonate, polypropylene, polyethylene, polystyrene, polyvinyl chloride, fluorinated ethylene polymer (FEP), polysulfone, polytetrafluoroethylene (PTFE), and the like.

Figure 2:
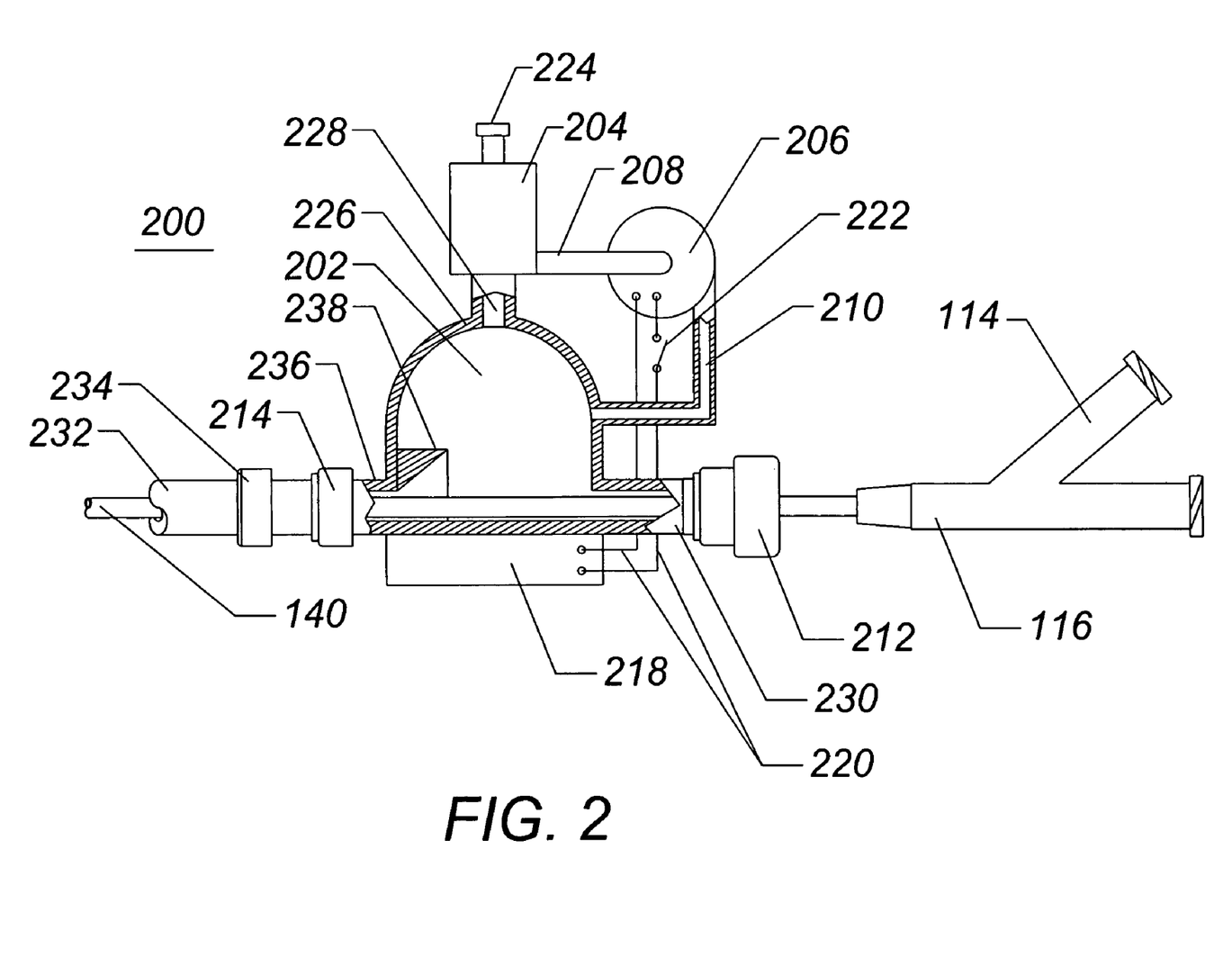
FIG. 2 illustrates a breakaway side view of a catheter air removal filter comprising a chamber, an external pump, an external gas separation chamber, and a liquid return line, according to an embodiment of the invention.

FIG. 2 illustrates a catheter blood air filter system 200 comprising a shell 226 comprising a chamber 202, an air vent port 228, a blood air separation chamber 204, a gas vent 224, a liquid return line 208, a motor driven pump 206, a pump return line 210, a second catheter inlet port 230, an inlet valve 212, an outlet valve 214, a first catheter 232, a first catheter connector 234, a second catheter outlet port 236, a battery 218, an electrical bus 220, an on-off switch 222, and a second catheter 116, further comprising a hub 114 and a second catheter shaft 140.

The air vent port 228 is affixed to the shell 226 and is operably connected to the chamber 202 at or near the top of the chamber 202. The gas vent 224 is affixed to the top of the blood air separation chamber 204, which is affixed to the air vent port 228. The inlet side of the liquid return line 208 is affixed at or near to the bottom of the blood air separation chamber 204. The outlet side of the liquid return line 208 is affixed to the motor driven pump 206. The motor driven pump 206 is operably connected to the battery 218 by the electrical bus 220 and the on-off switch 222 is operably connected to the electrical bus 220 to provide a means for turning the motor driven pump 206 on and off. The outlet of the motor driven pump 206 is physically and operably connected to the inlet of the pump return line 210. The outlet of the pump return line 210 is physically affixed to the shell 226 and operably connected to the chamber 202.

The second catheter inlet port 230 is affixed to the shell 226 and comprises a central lumen, which is operably connected to the chamber 202 near the bottom of the chamber 202. The inlet valve 212 is affixed to the second catheter inlet port 230 and comprises a central lumen operably connected to the central lumen of the second catheter inlet port 230. The second catheter outlet port 236 is affixed to the shell and further comprises a lumen that is operably connected to the chamber 202 near the bottom. The second catheter outlet port 236 is affixed to the outlet valve 214 and to the first catheter connector 234. The first catheter connector 234 is affixed or reversibly coupled to the first catheter 232. The second catheter outlet port 236 can comprise a funnel-shaped or beveled entrance, or other type of guide structure 238, to coerce the second catheter shaft 140 to becoming coaxially aligned, should the second catheter shaft 140 become bent out of the axis slightly during insertion.

The shell 226 and other components of the blood air filter system 200 can be fabricated from the same materials as those used in the embodiment 100 shown in FIGS. 1A and 1B. The sizes and flow rates of the two systems 100 and 200 are also similar. The wall thickness of the shell 226, and the shell of all devices disclosed herein, can range between about 0.010 inches and 0.125 inches with a preferred range of about 0.030 inches and 0.090 inches. The shell 226, as well as the shell of all devices disclosed herein is beneficially small in size, lightweight, and is free from flexible attachments other than the catheter itself or any fluid drip lines associated therewith.

The method of operation of the blood air filter system 200 is that it can be affixed to the proximal end of the first catheter 232. It can be primed and purged of air with saline through the gas vent 224. The motor driven pump 206 is turned on with the on-off switch 210. Flow is generated within the system to pull liquid out of the chamber 202 through the air vent port 228, and then pump liquid back into the chamber 202 through the pump return line 210, wherein air will separate in the air separation chamber 204 due to buoyant effects. Since the air vent port 228 is at the top of the chamber 202 any air in the chamber will preferentially collect near the air vent port 228 and be withdrawn from the chamber 202. Blood and other liquids, separated from the air in the air separation chamber 204 are returned to the chamber 202 by the motor driven pump 206.

The motor driven pump 206 can operate at voltages ranging between 1.5 and 24 volts DC and preferably between 1.5 and 6 volts DC. The battery 218 can match the voltage needs of the motor driven pump 206 and can operate for periods of up to 12 hours, preferably at least up to 6 hours once switched on. The system 200 is preferably disposable and is provided sterile in aseptic packaging similar to that described for the filter system 100 of FIGS. 1A and 1B. The battery 218 can be rechargeable, or single use. The battery 218 can comprise chemistries including, but not limited to, lithium ion, nickel metal hydride, alkaline, nickel cadmium, and the like. In some embodiments, the on-off switch 210 can comprise a layer of electrically insulated material, such as, but not limited to, paper, cardboard, polyvinyl chloride, polyethylene, polypropylene, or the like, the insulated material being disposed between two electrical contacts that are spring biased toward each other. These embodiments provide generally automatic on once the filter system 200 is put into service. The switch 210 layer can further comprise a tab that is removed, along with the attached layer of electrically insulating material, prior to use of the filter system 200 such that once the tab (not shown) is removed, the switch contacts 210 move to the closed position and remain in electrical contact until the battery 218 loses its charge or becomes depleted. The tab can be removed manually or it can be affixed to the packaging such that once the filter system 200 is removed from its sterile package, the on-off switch 210 is engaged. The on-off switch 210 can also comprise a toggle switch, rocker switch, or other design that is manually engaged by the user. Such power sources and automatic or manual switching can be used for all the embodiments of catheter air filters described herein.

Figure 3:
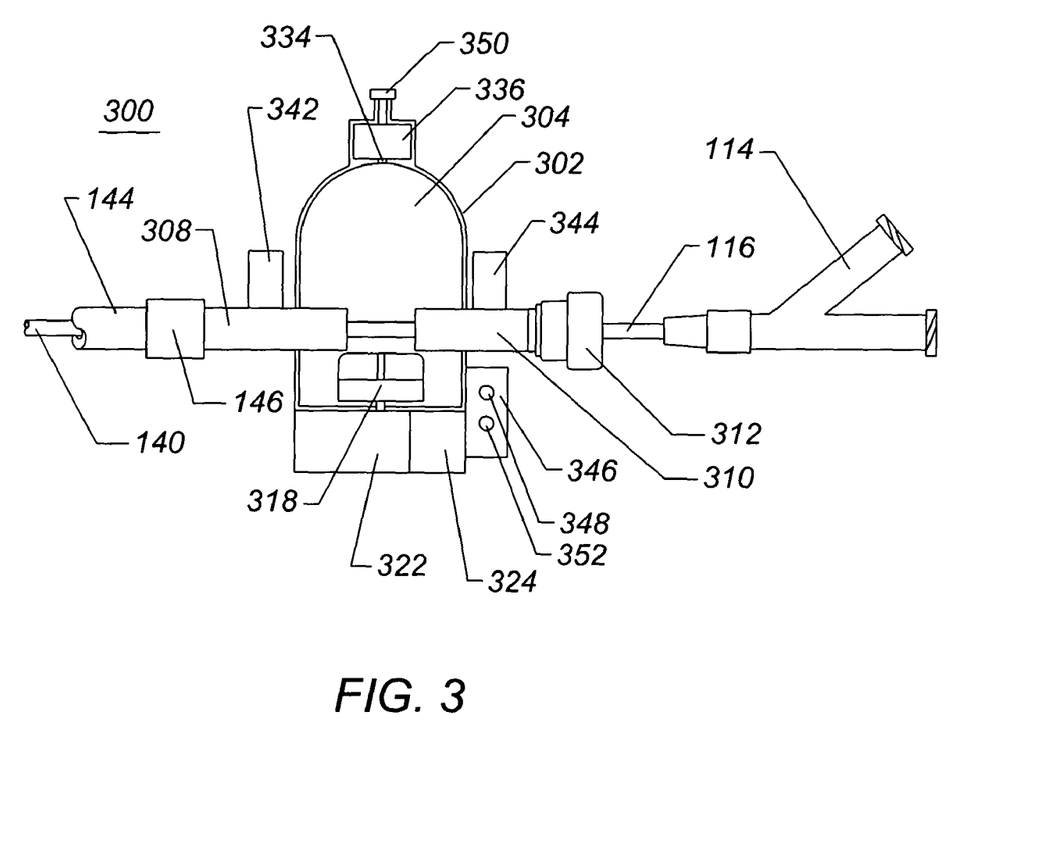
FIG. 3 illustrates breakaway side view of a catheter air removal filter comprising ultrasound transducers to detect air within the system, according to an embodiment of the invention.

FIG. 3 illustrates a blood air filter system 300 comprising ultrasound transducers 342 and 344 to detect the presence of air within the system 300. The blood air filter system 300 comprises a shell 302 enclosing a chamber 304, a gas exit port 334, a gas reservoir 336, a gas removal and purge port 350, a second catheter inlet port 310, a second catheter outlet port 308, a first catheter connector 146, a first catheter or sheath 144, a motor drive 322, an impeller 318, a battery pack 324, an inlet hemostasis valve 312, an ultrasound detection control system 346, at least one warning light 348, and a warning audible signal 352. The system 300 further comprises a second catheter 116 further comprising a hub 114 and a second catheter shaft 140.

Referring to FIG. 3, the blood air filter system 300 operates similarly to the filter system 100 described in FIGS. 1A and 1B except that the axis of the chamber is aligned vertically and the second catheter inlet port 310 and second catheter outlet port 308 are disposed on one side of the chamber 304 so that the vortex or circular flow field generated by the impeller 318 within the shell 304 forces any air or bubbles toward the central axis of the chamber 304 where it can rise to the top and be removed out the gas exit port 334 and into the gas reservoir 336.

The ultrasound transducers 342 and 344 can be affixed to the second catheter outlet port 308 and the second catheter inlet port 310, respectively and can detect the presence of air or gas in the system, which is normally supposed to be filled only with liquid (blood, saline, etc.). Ultrasound signals can pass easily through liquids but they do not travel through gas well, so discrimination of the two phases is easily accomplished with ultrasound transducers. The ultrasound transducers 342 and 344 are wired to the ultrasound control unit 346 by an electrical bus (not shown). Power can be derived from the battery 324 or from another battery (not shown). The ultrasound control unit can display the presence of air by illuminating the warning light 348, sounding the audible signal 352, or both. Each transducer 342 and 344 can, in another embodiment, have a separate warning light, audible warning frequency, or both. Another ultrasound transducer (not shown) can be used to detect significant buildup of gas in the gas reservoir 336 such that the gas can be removed through the purge port 350.

Figure 4:
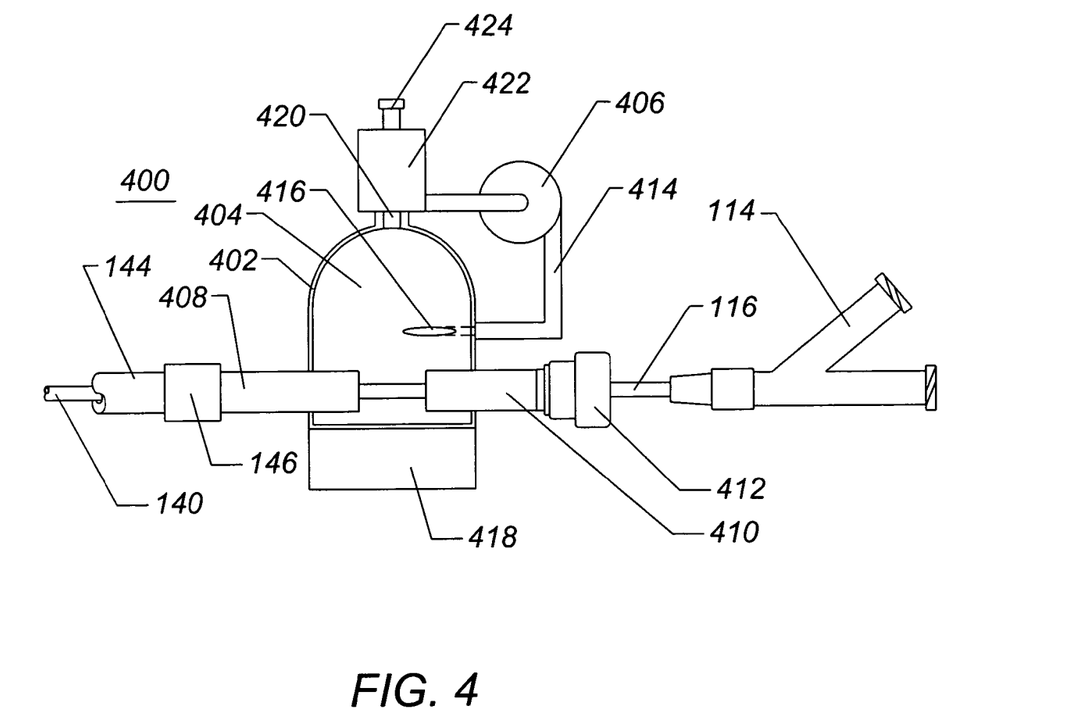
FIG. 4 illustrates breakaway side view of a catheter air removal filter comprising a chamber configured to generate circular flow of liquid therein, wherein the circular flow is generated by an external pump and a tangential fluid return line into the chamber, according to an embodiment of the invention.

FIG. 4 illustrates a catheter blood air filter system 400 comprising a shell 402, which encloses an axially elongate chamber 404. The filter 400 system further comprises a motor driven pump 406, a second catheter outlet port 408, a second catheter inlet port 410, an inlet valve 412, a liquid return line 414, a tangential liquid return line inlet 416 to the chamber 404, a power source 418, a gas vent 420, a gas collection chamber 422, a gas bleed and purge port 424, a first catheter or sheath 144, a first catheter or sheath connector 146, and a second catheter 116 further comprising a hub 114 and a second catheter shaft 140.

Referring to FIG. 4, the gas vent 420 is affixed to the top of the shell 402. The chamber 404 is generally cylindrical and axially elongate but the top of the chamber 404 can beneficially be tapered or rounded to funnel air toward the center as it rises. The gas collection chamber 422 is affixed to the gas vent 420 or the shell 402 and the internal volume of the gas collection chamber 422 is operably connected to the lumen of the gas vent 420. The inlet to the motor driven pump 406 is affixed near the bottom of the gas collection chamber 422. The liquid return line 414 is affixed to the outlet of the motor driven pump 406. In this and the other embodiments requiring an external pump, the motor driven pump 406 can be a centrifugal pump, as illustrated, or it can be a roller pump, a piston pump, a diaphragm pump, or the like.

Fluid being pumped back into the chamber 404 through the return inlet line 416 forms a fluid jet which, directed tangentially along the wall of the chamber 404, generates a circular flow pattern or vortex within the chamber 404. This circular flow pattern entrains air and bubbles toward the center due to the effects of air buoyancy acting in a centrifugal flow field. Thus air is moved away from the second catheter inlet port 410 and the second catheter outlet port 408, both of which are affixed to the shell 402 near the bottom and near the periphery of the chamber 402. Air can be entrained into the chamber 404 by insertion of the second catheter shaft 140 through the inlet valve 412, which is a hemostasis type valve as described in the embodiment shown in FIGS. 1A and 1B, at the inlet to the chamber 404 if the hemostasis valve 412 leaks or becomes faulty.

Figure 5:
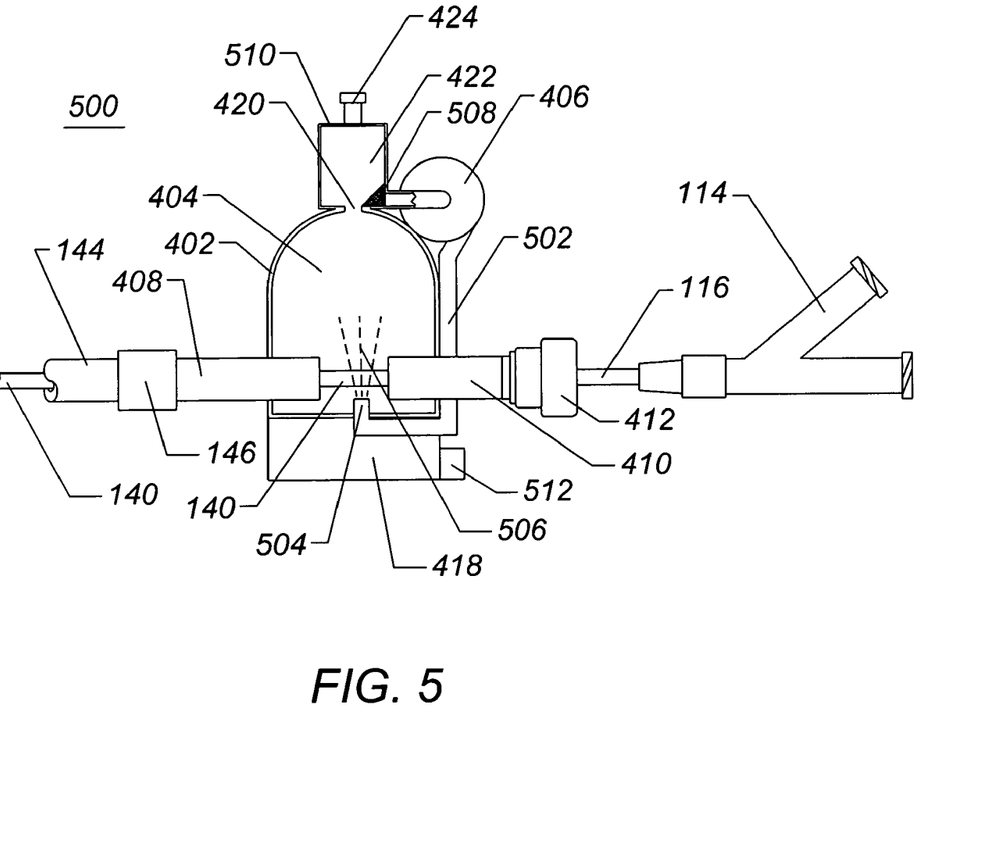
FIG. 5 illustrates a breakaway side view of a catheter air removal filter comprising a chamber configured to scrub a catheter shaft inserted therethrough by means of a fluid jet emanating from the outlet of the fluid return line from an external liquid pump, according to an embodiment of the invention.

FIG. 5 illustrates a breakaway side view of a catheter air removal filter system 500 comprising a shell 402 enclosing a chamber 404. The filter system 500 system further comprises a motor driven pump 406, a second catheter outlet port 408, a second catheter inlet port 410, an inlet valve 412, a liquid return line 502, a liquid return line inlet 504 to the chamber 404, a power source 418, an on-off switch 512, a gas vent 420, a gas collection chamber 422, a gas collection chamber case 510, a gas bleed and purge port 424, a particulate filter 508, a first catheter or sheath 144, a first catheter or sheath connector 146, and a second catheter 116 further comprising a hub 114 and a second catheter shaft 140. Liquid entering the chamber 404 is in the form of a fluid jet 506 capable of scrubbing the catheter shaft 140.

Referring to FIG. 5, the liquid return line 502 is generally routed near to, against, or integral to the chamber shell 402. The motor driven pump 406 is affixed to the shell 402, as is the case 510 of the gas collection chamber 422. The components are all rigidly, or semi-rigidly, affixed to the shell 402 to minimize bulk and to make the system easily maneuverable without excess weight, or dangling components. There is no requirement for a lead line to a reservoir of fluid (not shown). Such a drip line to a reservoir can be added for the purpose of adding heparinized saline to the system but is not required for the function of the filter system 500. Such drip lines (not shown) are often comprised by the hub 114 of the second catheter 116 but are not the subject of this disclosure. The interior components of the filter system 500 can comprise coatings that comprise anti-thrombogenic properties.

The motor driven pump 406 can, in certain embodiments, serve to withdraw liquid from the distal end of the first catheter or sheath 114 all the way back to the gas collection chamber 422 where it can be removed from the system through the gas bleed 424. The power source 418 can be affixed directly to the shell 402 to minimize bulk. The on-off switch 512 for the motor driven pump 406 can be a separate on-off or on switch that runs until the battery power source 418 is depleted of energy. The on-off switch 512 can further be embedded within the second catheter inlet port 410, the second catheter outlet port 408. The on-off switch 512 can further be a light activated, ultrasonically activated by ultrasound transducers 342, 344, such as those described in FIG. 3, or pressure activated device associated with the filter system 500. The ultrasound transducers 342, 344 can be affixed to the shell 402, the second catheter inlet port 410, the second catheter outlet port 408, or both. The weight of the filter assembly 500 should be less than 450 grams and preferably less than 200 grams. The size of the filter assembly 500 or any of the other filter systems described herein is ideally less than approximately 5-cm in any direction or side dimension, including all components, to minimize bulk and maximize maneuverability of the first catheter 144 and second catheter 116. The filter assemblies 500, 400, 300, 200, or 100 can further be configured to permit a plurality of second catheter inlet ports 410 so the filter assemblies can be part of a second catheter hub Y connector, for example.

The gas purge port 424 can be monitored by an ultrasonic transducer to detect the presence of gas in the collection chamber 422 and audibly or visually signal the need to remove the gas. The gas purge port 424 can be terminated by a stopcock or other valve, such that application of a syringe or hypodermic needle can permit the removal of collected gas or air. The gas purge port 424 can further be interconnected to a pump system that automatically, or manually, actuates removes collected gas.

Figure 6A:
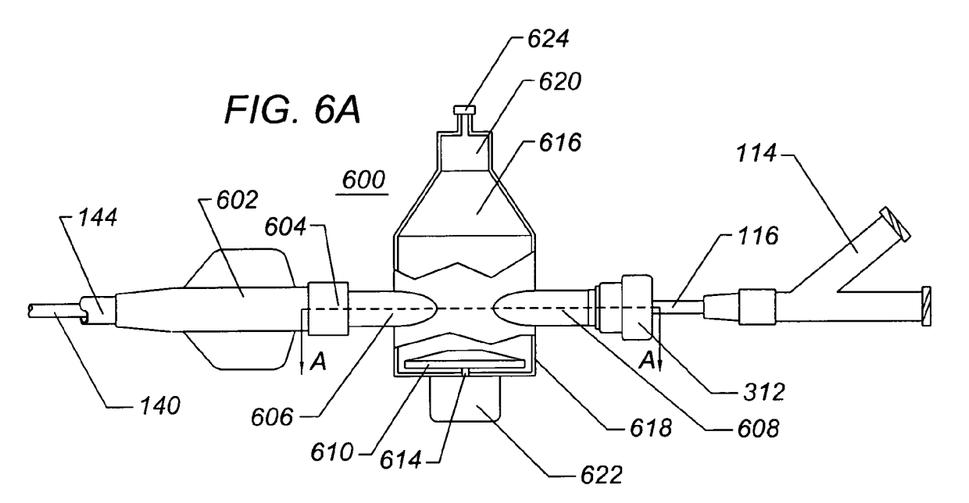
FIG. 6A illustrates a breakaway side view of a catheter air removal filter comprising a chamber, a rotary impeller, and a motor drive wherein the filter is affixed to the proximal end of a guide catheter, sheath, or cannula, according to an embodiment of the invention.

FIG. 6A illustrates a catheter, cannula, sheath, or introducer blood air filter 600 comprising a shell wall 618 and a central volume 616, an air collection region 620, an air bleed port 624, an impeller 610, an impeller shaft 614, a motor drive 622, an inlet port 608, an outlet port 606, a sheath connector 604, an inlet valve 312, an introducer, cannula, sheath, or first catheter 144 further comprising a cannula hub 602, and a second catheter 116 further comprising a hub 114 and a second catheter shaft 140. The filter 600 further comprises a power supply (not shown), an on off switch (not shown), an impeller shaft seal (not shown) and an electrical bus (not shown).

Referring to FIG. 6A, the impeller 610 is affixed to the impeller shaft 614, which is affixed to the rotational part of the motor drive 622. The impeller 610 rotates about its central axis, which is concentric and parallel with the impeller shaft 614. The impeller 610, as illustrated is a shear impeller and does not have vanes or other projections. The shear impeller is generally smooth with no substantial radial or spiral projections from its structure. While a shear impeller is not as efficient at spinning fluid as a vane impeller, the shear impeller causes less damage to the red and white blood cells than does the vane impeller. Rotation of the shear impeller 610 imparts a circular motion of fluid (generally blood and saline), generated by viscous or inertial forces, within the central volume 616 with the circular motion directed about the central axis of the impeller 610. Centrifugal forces cause the blood and liquid within the chamber to move outward and any air or gas to move inward toward the center of the central volume 616. Collected air within the air collection region 620 can be removed through the gas or air bleed port 624. The gas or air bleed port can comprise a bayonet, threaded, or Luer fitting, or it can further comprise a valve system (not shown) such as a stopcock, one way valve, or the like. There is beneficially no valve associated with the outlet port 606 but any valves so integrated need to permit retrograde flow in the proximal direction because the system is primed through the lumen of the cannula or sheath 144 by fluids from the vascular system.

The filter 600 can be releasably affixed to the hub 602 of the cannula or first catheter 144 by means of a Luer lock 604, bayonet mount, threaded fitting, or the like. The Luer lock 604 is affixed to the distal end of the outlet port 606. The inlet port 608 is affixed to the hemostasis valve 312, which can comprise a duckbill valve, a Tuohy-Borst valve, a pinhole valve, a slit valve, a combination thereof, or similar. The motor drive 622, the shell 618, the impeller 610, and other components of the system can be fabricated from materials similar to those used for the filter embodiments illustrated in FIGS. 1A-5. In the illustrated embodiment, the upper region of the shell 618 tapers inward toward the air collection chamber 620. In other embodiments, different geometries such as substantially non-tapered walls or substantially outwardly tapered walls may be advantageous.

Figure 6B:
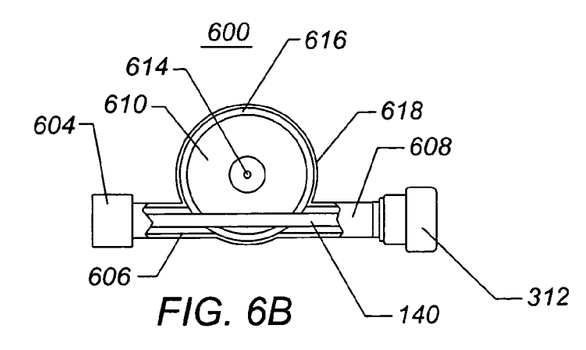
FIG. 6B illustrates a lateral sectional view of the filter of FIG. 6A showing the circular internal geometry and off-center disposition of the catheter access ports, according to an embodiment of the invention.

FIG. 6B illustrates a lateral cross-sectional view of the filter 600 of FIG. 6A, looking toward the bottom or motor drive 622 end along the line A-A. The filter 600 comprises the shell wall 618, the inlet port 608, the outlet port 606, the inlet valve 312, the outlet connector 604, the impeller 610, the impeller shaft 614, and the shaft or tubing 140 of the second catheter 116. The central volume 616 is generally cylindrical in shape, as illustrated in this sectional view. The cylindrical shape can also comprise an hourglass, a trapezoid tapering downward, a trapezoid tapering upward, or complex geometries, all of which are substantially circular in cross-section. The circular cross-sectional shape permits the blood or liquid to flow in a circular pattern to the maximum achievable rotational velocity. The second catheter shaft 140 is disposed near the periphery of the shell 618 such that any air introduced thereby is forced toward the center of the chamber 616 and away from the outlet port 606.

Figure 7:
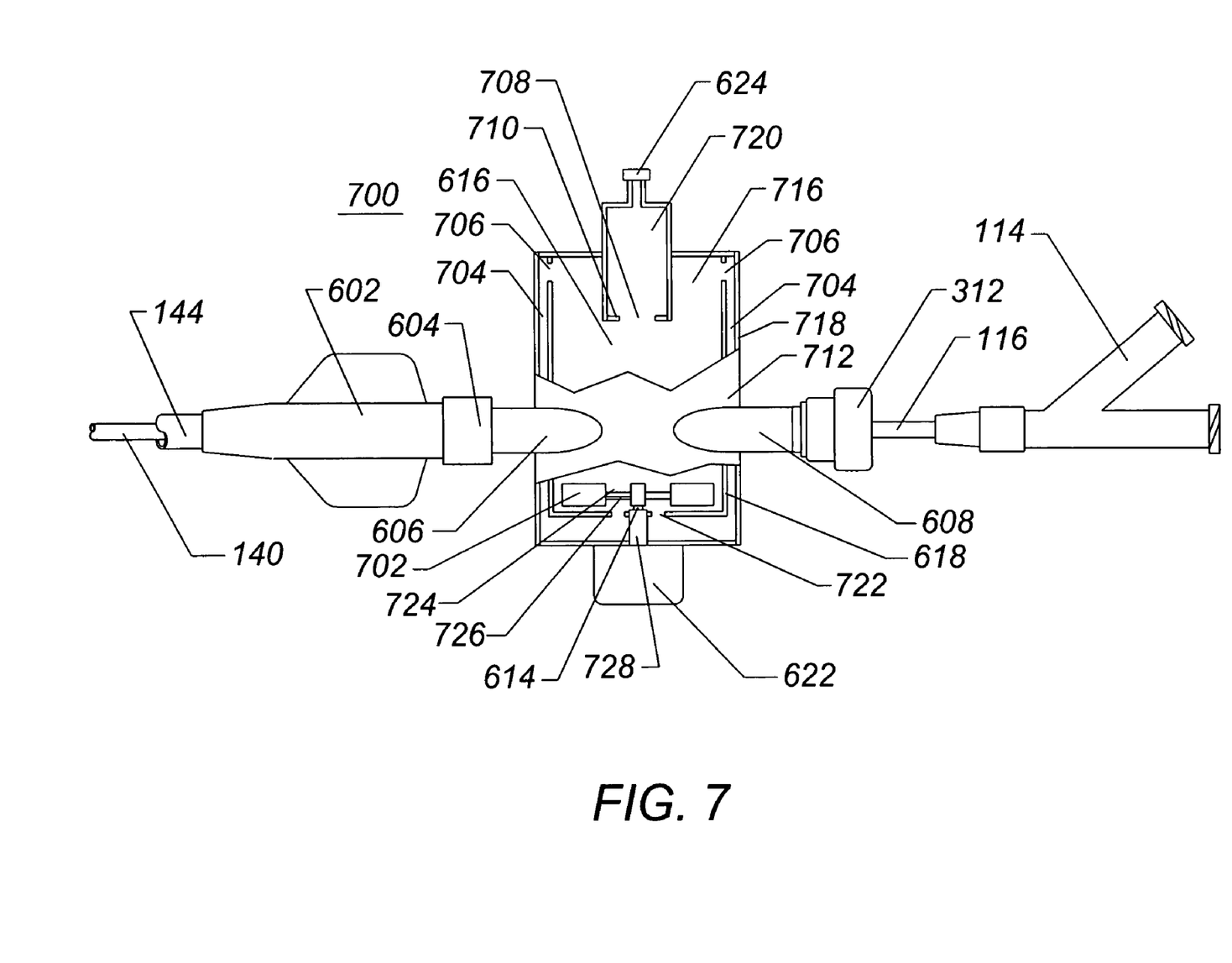
FIG. 7 illustrates a lateral, partial breakaway view of a catheter, sheath, introducer, or cannula air filter wherein the filter comprises a flow through impeller that not only spins the blood but also provides pumping action to circulate the blood through return ducts connecting one end of the filter with the other end, according to an embodiment of the invention.

FIG. 7 illustrates a partial breakaway side view of another embodiment of a catheter, sheath, cannula, or introducer air filter 700. The filter 700 comprises the inlet port 608, the inlet valve 312, the outlet port 606, the outlet port connector 604, an outer shell 712, the inner shell 618 further comprising the chamber 616 and the upper chamber 716, a plurality of return inlet ducts 704, a plurality of return duct inlet ports 706, the motor drive 622, an impeller seal 728, the impeller shaft 614, the impeller 702 further comprising flow through vents 724 and propeller or fan blades 726, a plurality of return duct outlet ports 722, the air vent 624, an air collection chamber 720, an air collection chamber inlet port 708, and an air collection chamber baffle 710. Affixed to the filter 700 are the cannula, sheath, introducer, or first catheter 144 further comprising the hub 602, and the second catheter 116 further comprising the second catheter shaft 140 and the second catheter hub 114.

Referring to FIG. 7, the outlet connector 604 is releasably affixed to the first catheter hub 602 but can also be permanently affixed thereto if desired. The second catheter shaft 140 is inserted through the inlet valve 312. The impeller 702 comprises holes or fenestrations 724 that permit blood to flow through the impeller 702 and into the chamber volume from the return ducts 704. The spinning impeller 702 creates high fluid pressure near the periphery of the inner shell 618 and low pressure near the central axis. Thus blood entering near the central axis through the return duct outlet ports 722 enters the chamber 616, flows upward toward the upper chamber 716, and exits via the return duct inlet ports 706 with a circulation setup thereby. Flow within the chamber 618 is circular as driven by the impeller 606 and moves from the bottom end, near the motor drive 622 toward the top end nearest the air collection chamber 720. Bubbles of air or gas are forced toward the central axis by centrifugal effects and enter the air collection chamber 720 where they can be withdrawn through the air vent 624. The air collection chamber 720 is beneficially fabricated from transparent materials so that collected air can be visualized and removed. A bubble or gas detector (not shown), such as an ultrasonic probe with an alarm can be used to further indicate the presence of air in the system or in the air collection chamber 720. By setting up both a bottom to top flow as well as a rotational flow, the system becomes independent of gravitational orientation and can function no matter in which direction the central axis is aligned. The materials of fabrication, motor specifications, rotation rates, etc. are consistent with other filter embodiments described herein.

Figure 8:
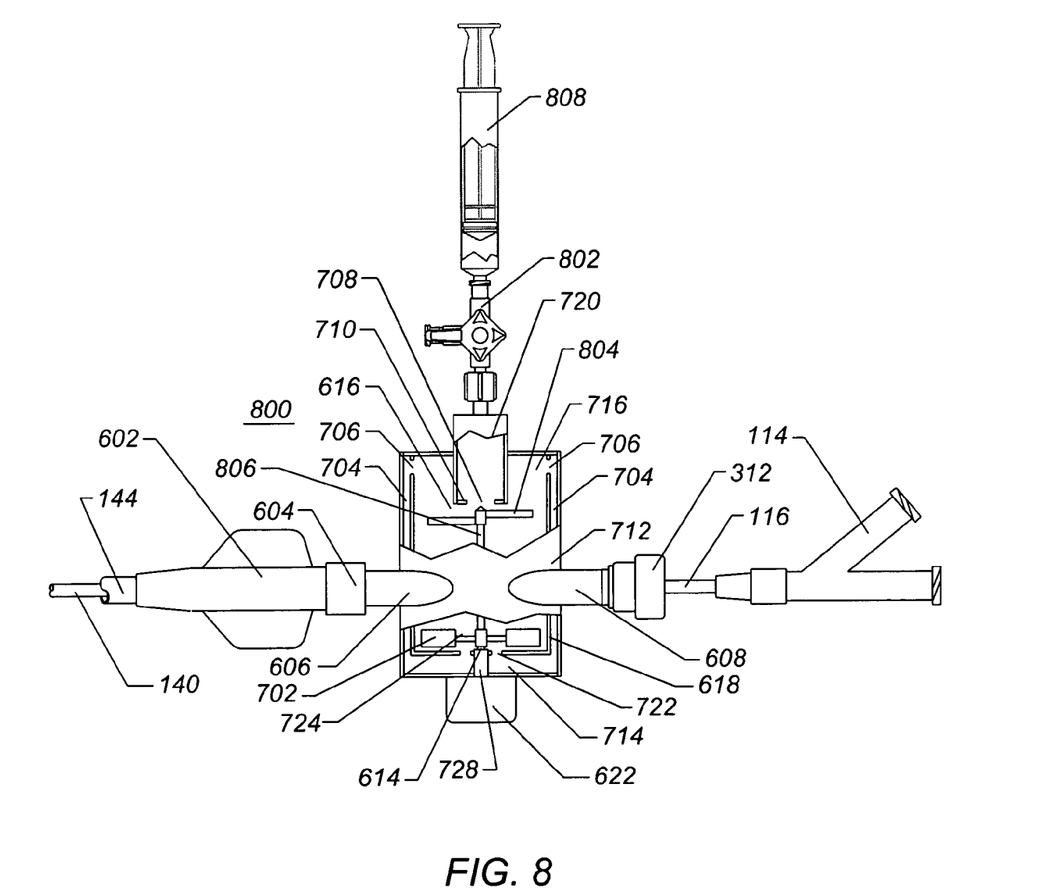
FIG. 8 illustrates a lateral, partial breakaway view of a catheter, sheath, introducer, or cannula air filter comprising a two-stage impeller that spins the blood and pumps the blood, an air trap chamber, and an air removal device, according to an embodiment of the invention.

FIG. 8 illustrates an air trap or filter 800 affixed to the hub 602 of a first cannula, sheath, introducer, or catheter 144. The air trap 800 comprises the inlet port 608, the inlet valve 312, the outlet port 606, the outlet port connector 604, an outer shell 712, the inner shell 618 further comprising the chamber 616 and the upper chamber 716, a plurality of return inlet ducts 704, a plurality of return duct inlet ports 706, the motor drive 622, an impeller seal 728, the impeller shaft 614, the impeller 702 further comprising flow through vents 724, a plurality of return duct outlet ports 722, the air vent 624, an air collection chamber 720, an air collection chamber inlet port 708, and an air collection chamber baffle 710. Inserted through the filter 800 is the second catheter 116 further comprising the second catheter shaft 140 and the second catheter hub 114. The impeller shaft 614 further comprises an extension 806 and an upper propeller 804 configured to move blood from the bottom to the top of the chamber 616. Affixed to the gas outlet port 624 (FIG. 6A) of the gas collection chamber 720 is a stopcock 802 and a syringe 808 for withdrawal of gas or air.

Referring to FIG. 8, the propeller 804 moves blood, liquid, and gas toward the top of the system while the impeller 702 establishes and maintains circular flow to accelerate air and bubbles toward the axis of the system. The syringe is one way to remove air although an automated gas venting system can also be used. The stopcock 802 can be used to close the gas removal port 624 while the syringe 808 is being emptied of air.

Figure 9:
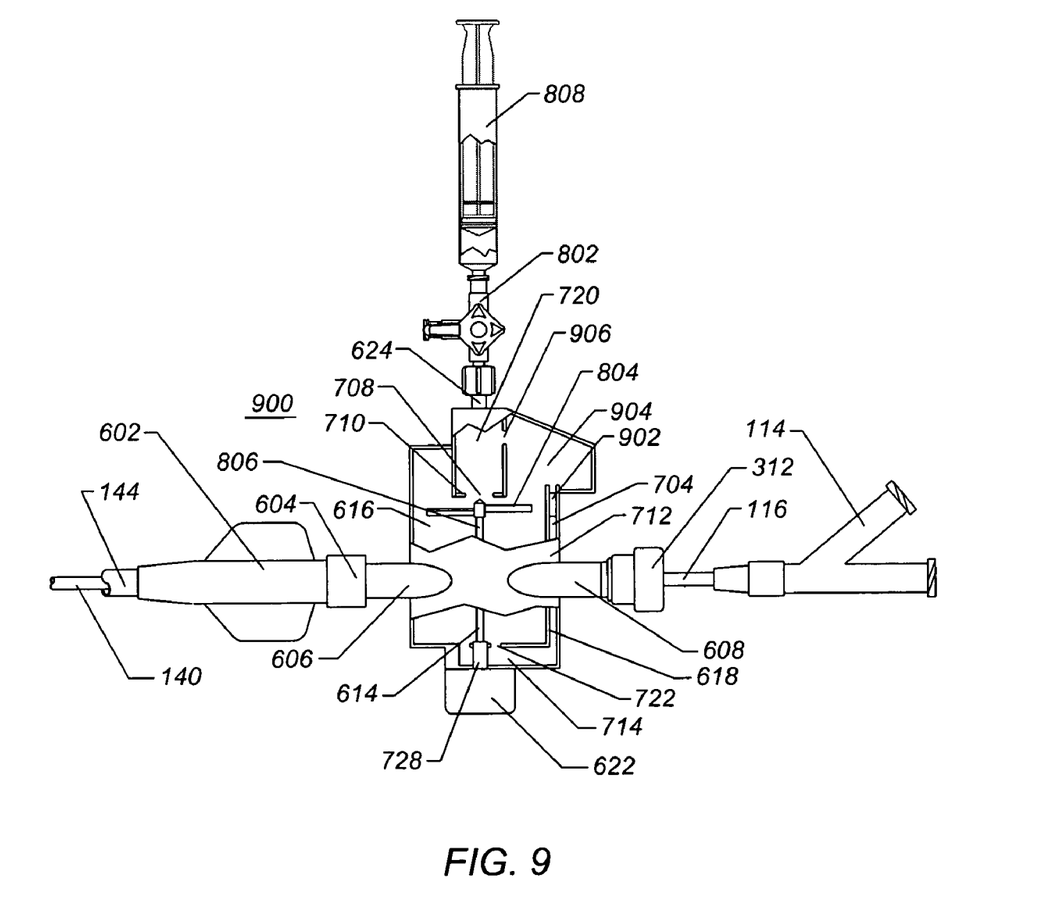
FIG. 9 illustrates a lateral, partial breakaway view of a catheter, sheath, introducer, or cannula air filter comprising a pumping impeller disposed downstream of the catheter introduction region, a central air trap, and an air filter to remove air from blood returned to the bottom of the filter by means of the return ducts, according to an embodiment of the invention.

FIG. 9 illustrates an air trap or filter 900 affixed to the hub 602 of a first cannula, sheath, introducer, or catheter 144. The air filter or trap 900 comprises the inlet port 608, the inlet valve 312, the outlet port 606, the outlet port connector 604, an outer shell 712, the inner shell 618 further comprising the chamber 616, the return duct 704, a bubble mesh or membrane filter element 902, the motor drive 622, the impeller seal 728, the impeller shaft 614, further comprising the extension 806, the propeller 804, the return duct outlet port 722, the air vent 624, an air collection chamber 720, an air collection chamber inlet port 708, and an air collection chamber baffle 710. Inserted through the filter 900 is the second catheter 116 further comprising the second catheter shaft 140 and the second catheter hub 114. The impeller shaft 614 further comprises an extension 806 and the upper propeller 804 configured to move blood from the bottom to the top of the chamber 616. Affixed to the gas vent 624 (FIG. 6A) of the gas collection chamber 720 is a stopcock 802 and a syringe 808 for withdrawal of gas or air. The air collection chamber 720 further comprises an upper access port 906. The inner chamber 616 further comprises a residual gas collection plenum 904.

Referring to FIG. 9, blood flowing through the return duct 704 passes through the filter element 902, which comprises a mesh or membrane having pores of about 20 to 50 microns in size such that large bubbles will catch therein and not pass through due to surface tension effects. The residual gas collection plenum 904 routes gas that is prevented from passing the mesh filter element 904 back into the gas collection chamber 720 through the upper access port 906. The propeller 806 serves to pump liquid and air upward away from the motor drive 622 end and toward the gas collection chamber 720 but also serves to impart rotational flow within the chamber 616. Rotational rates, materials of fabrication, sizes, and specifications are similar to other embodiments described herein.

Figure 10:
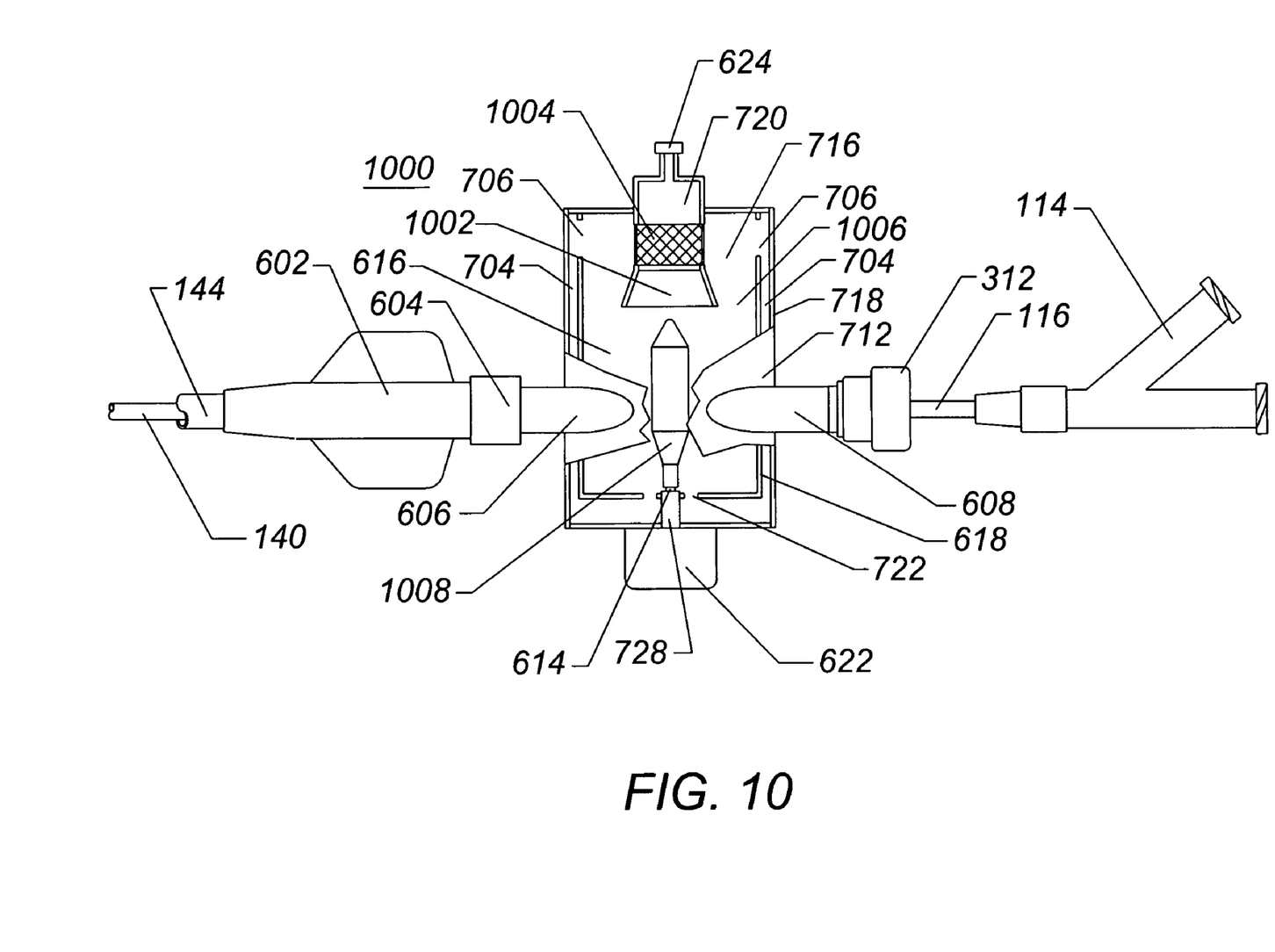
FIG. 10 illustrates a lateral, partial breakaway view of a catheter, sheath, introducer, or cannula air filter comprising a narrow, shear impeller, one or more return ducts, a central air trap, and a mesh or membrane air separation filter disposed around the air trap, according to an embodiment of the invention.

FIG. 10 illustrates a partial breakaway side view of another embodiment of a catheter, sheath, cannula, or introducer air filter 1000. The filter 1000 comprises the inlet port 608, the inlet valve 312, the outlet port 606, the outlet port connector 604, an outer shell 712, the inner shell 618 further comprising the chamber 616 and the upper chamber 716, a plurality of return inlet ducts 704, a plurality of return duct inlet ports 706, the motor drive 622, an impeller seal 728, the impeller shaft 614, an elongate impeller 1008, a plurality of return duct outlet ports 722, the air vent 624, an air collection filter wall 1004, an air collection chamber inlet port 1002. Affixed to the filter 700 are the cannula, sheath, introducer, or first catheter 144 further comprising the hub 602. The tubing or shaft 140 of the second catheter 116 further comprising the second catheter hub 114 is inserted through the inlet 608 and outlet 606 ports of the filter 1000.

Referring to FIG. 10, the elongate impeller 1008 spins the fluid or blood through shear effects while minimizing potential blood damage. The pressure drop generated across the chamber 616 causes blood to flow from the return duct outlet ports 722 through the chamber 616 and exits through the return duct inlet ports 706 to the return ducts 704. Gas, air, and bubbles are forced centrally by the rotational flow generated inside the chamber 616 by the shear impeller 1008 and forced into the air collection chamber 720 where they can be removed through the gas vent 624. Blood and liquid can flow out through the air collection filter wall 1004 and into the upper chamber 716 where it can return to the bottom of the chamber 616 through the return ducts 704. The narrow, axially elongate impeller 1008 permits fluid to flow around it without the need for perforations or holes therein.

Other aspects of the inventions include methods of use. In an exemplary embodiment, a sheath, such as a Mullins sheath is used to access the left atrium of the heart by way of femoral venous access via the Seldinger technique or similar. The Mullins-type sheath is advanced through the inferior vena cava into the superior vena cava. A transseptal needle, such as a Brockenbrough needle, is inserted through the Mullins-type sheath or catheter and aligned medially. The transseptal needle and sheath combination is withdrawn from the superior vena cava into the right atrium where the catheter, protecting the tip of the needle engages the fossa Ovalis. The needle is advanced out through the distal end of the Mullins-type sheath and through the fossa Ovalis. The Mullins sheath is advanced over the transseptal needle into the left atrium. The transseptal needle is removed and therapeutic or diagnostic catheters are inserted through the Mullins-type sheath into the left atrium. Procedures such as electrophysiology mapping, electrophysiology ablation of the heart, atrial appendage procedures including plugs, filters, and closure devices, mitral valve procedures., and the like can be performed through such an access procedure. The application of the air filter, described herein, to the proximal end of the Mullins-type sheath would significantly reduce the risk of air embolism in these procedures. The left atrium can expose the distal end of the catheter to low enough pressures to draw air into the left atrium through an inserted catheter, thus the need for such a prevention device. Other procedures where such an air embolism protection device would be beneficial includes central venous access catheters, cardiac access catheters and catheters used for cerebrovascular access.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A method for preventing gas from entering a catheter, wherein the catheter interior is exposed to blood or other liquid, said method comprising:

affixing an axially elongate shell at or near the proximal end of a first catheter, wherein said shell comprises a chamber having a centerline;

rotating an impeller about or near the centerline of the chamber, wherein said rotation of said impeller directly imparts rotational energy to a fluid within the chamber causing any gas collected within the chamber to migrate toward the centerline;

removing the gas from the chamber through a gas removal port near the centerline of said shell;

affixing a catheter inlet port to the shell near a periphery of said chamber, said catheter inlet port operably connected to the chamber;

affixing a catheter outlet port near the distal end of the shell, said catheter outlet port being affixed, and operably connected to the proximal end of the first catheter, and near a periphery of said chamber, wherein the catheter inlet port is coaxially aligned with the catheter outlet port;

inserting a second catheter through the catheter inlet port, through the chamber, through the catheter outlet port, through the first catheter, and on into the cardiovascular system of a patient; and separating any liquid removed from the chamber from the gas.

2. The method of claim 1, wherein said impeller is spun at a rate of between about 100 to 1,000 revolutions per minute.

3. The method of claim 1, wherein the impeller is rotated by an electric motor.

4. The method of claim 1 further comprising the step of affixing a valve to the catheter inlet port to substantially prevent air or other gas from entering the chamber from an outside room environment.

5. The method of claim 1 further comprising the step of affixing a hemostasis valve to the catheter outlet port to substantially prevent air or other gas from entering the first catheter from the chamber.

6. The method of claim 1 further comprising the step of pumping the blood and other liquid, along with any air entrained within a central vortex, toward an end of the chamber where the air can be drawn off into the gas removal port.

7. The method of claim 6 wherein the pumping step is performed by rotating the impeller.

8. The method of claim 1 further comprising the step of returning the liquid to the chamber through a return line.

* * * * *